(12) United States Patent
John

(10) Patent No.: US 8,287,920 B2
(45) Date of Patent: Oct. 16, 2012

(54) METHOD AND COMPOSITION FOR TREATMENT OF YEAST INFECTION THROUGH A RADIAL APPLIANCE OR A WET-CELL BATTERY APPLIANCE AND SOLUTION JAR SET

(76) Inventor: Beth John, West Babylon, NY (US)

( * ) Notice: Subject to any disclaimer, the term of this patent is extended or adjusted under 35 U.S.C. 154(b) by 378 days.

(21) Appl. No.: 12/403,888

(22) Filed: Mar. 13, 2009

(65) Prior Publication Data

US 2010/0233284 A1 Sep. 16, 2010

(51) Int. Cl.
*A61K 36/00* (2006.01)
*A61K 36/8962* (2006.01)
*A61K 36/064* (2006.01)

(52) U.S. Cl. ............... 424/725; 424/754; 424/93.51

(58) Field of Classification Search .............. None
See application file for complete search history.

(56) References Cited

U.S. PATENT DOCUMENTS 3,471,615 A * 10/1969 Chandler, Jr. et al. ........ 514/690

OTHER PUBLICATIONS

Natural Candida Cure: Candida Albicans Cure; Archived to Oct. 17, 2007, online, URL<http://replay.waybackmachine.org/20071017031208/http://www.candida-albicans-cure.com/natural-candida-cure.html>, pp. 1-4.*
1 Bruce Baar, Experience . . . The Radiac, 2007, 93pp., Bear Products, Inc. Downingtown, PA.

* cited by examiner

*Primary Examiner* — Patricia Leith
(74) *Attorney, Agent, or Firm* — The Farrell Law Firm, P.C.

(57) ABSTRACT

Provided are a composition and method of increasing health of the human body includes placing a composition inside a solution jar of a solution jar assembly, wherein the composition comprises at least one of a garlic solution comprising garlic extract, ethanol, and water; a 10-undecenoic acid solution comprising 10-undecenoic acid and at least one of water and alcohol; and a Pau d'Arco solution comprising Pau d'Arco extract, corn starch, ethanol, and water, wherein the solution jar assembly includes a device comprising either a radial appliance or a wet-cell battery appliance; a first metal disc connected to the device by a first wire; a solution jar, connected to the device by a second wire, for holding the solution; a second metal disc connected to the solution jar by a third wire; and a connecting loop, located inside a removable lid of the solution jar, connecting the first and third wires and passing through the solution; wherein if the device is the radial appliance, placing the radial appliance in a container having ice and water; and applying the first and second discs to skin of a human body.

15 Claims, 2 Drawing Sheets

METHOD AND COMPOSITION FOR TREATMENT OF YEAST INFECTION THROUGH A RADIAL APPLIANCE OR A WET-CELL BATTERY APPLIANCE AND SOLUTION JAR SET

BACKGROUND OF THE INVENTION

1. Field of the Invention

The present invention relates generally to a composition and method for administration of a solution to a user using either a radial appliance or a wet cell battery appliance.

2. Description of the Related Art

The radial appliance (also commonly referred to as a "radio-active appliance") and the wet-cell battery appliance are devices for balancing electric vibrations in a human body. When used in combination with a solution, typically presented in a jar set, properties of the vibrations may be altered by the solution.

FIG. 1 is a diagram of a conventional radial appliance and solution jar set. A radial appliance 110 is an apparatus typically composed primarily of a housing containing two metal rods packed in charcoal separated by glass plates (not shown). Construction of radial appliances is well-known in the art and therefore details thereof are omitted for clarity. The radial appliance 110 is connected to first and second wires 130 and 140, respectively. The first wire 130 is connected to a first metal disc 120, and the second wire 140 is connected to a solution jar 150.

The solution jar 150 includes a connecting loop 152 attached to a removable lid 151, and the solution jar 150 holds a solution 153, such that the connecting loop 150 is at least partially immersed in the solution 153. The second wire 140 and a third wire 160 are connected to the connecting loop 152 via the lid 151. A second metal disc 170 is connected to the third wire 160.

To use the radial appliance 110 and solution jar 150, the radial appliance 110 is placed at least partially immersed in ice and/or cold water (not shown) and the metal discs are placed into contact with the human body.

FIG. 2 is a diagram of a conventional wet-cell battery appliance for use with the solution jar set. The apparatus disclosed in FIG. 2 is the same as that of FIG. 1, except that the radial appliance 110 is replaced with a wet-cell battery appliance 210. The wet-cell battery appliance is connected to the first and second wires 130 and 140 in place of the radial appliance 110. The wet-cell battery appliance includes a battery solution 213, which typically includes water, copper sulphate, sulphuric acid, charcoal, and zinc. The wet-cell battery further includes two poles 211 and 212 at least partially immersed in the battery solution 213 and connected to the first and second wires 130 and 140 respectively. Construction of wet-cell battery appliances is well-known in the art and therefore further construction details thereof are omitted for clarity. The wet-cell battery 210 is used with the solution jar 150 in the same manner as the radial appliance 110 and the solution jar 150, as described hereinabove with reference to FIG. 1.

However, only a few solutions (e.g., including spirits of camphor, gold chloride, iodine, silver nitrate, etc.) have been disclosed for use with the solution jar, the disclosed solutions having a limited set of properties. Therefore, there is a need for other solutions and treatment methods using the radial appliance and the wet-cell battery appliance. In particular, there is a need for treatment of yeast and other fungal infections through use of the radial appliance and the wet-cell battery appliance.

SUMMARY OF THE INVENTION

Accordingly, the present invention has been made to solve the above-mentioned problems occurring in the prior art, and the present invention provides a composition and method for administration of a solution to a user using either a radial appliance or a wet cell battery appliance for treating yeast and other fungal infections.

According to one aspect of the present invention, a composition for administration, to a user, in a form of a solution via a solution jar assembly includes at least one of a garlic solution comprising garlic extract, ethanol, and water; a 10-undecenoic acid solution comprising 10-undecenoic acid and at least one of water and alcohol; and a Pau d'Arco solution comprising Pau d'Arco extract, corn starch, ethanol, and water, wherein the solution jar assembly includes a device comprising either a radial appliance or a wet-cell battery appliance; a first metal disc connected to the device by a first wire; a solution jar, connected to the device by a second wire, for holding the solution; a second metal disc connected to the solution jar by a third wire; and a connecting loop, located inside the solution jar, connecting the first and third wires and passing through the solution.

According to another aspect of the present invention, a method of increasing health of the human body includes placing a composition inside a solution jar of a solution jar assembly, wherein the composition comprises at least one of a garlic solution comprising garlic extract, ethanol, and water; a 10-undecenoic acid solution comprising 10-undecenoic acid and at least one of water and alcohol; and a Pau d'Arco solution comprising Pau d'Arco extract, corn starch, ethanol, and water, wherein the solution jar assembly includes a device comprising either a radial appliance or a wet-cell battery appliance; a first metal disc connected to the device by a first wire; a solution jar, connected to the device by a second wire, for holding the solution; a second metal disc connected to the solution jar by a third wire; and a connecting loop, located inside a removable lid of the solution jar, connecting the first and third wires and passing through the solution; wherein if the device is the radial appliance, placing the radial appliance in a container having ice and water; and applying the first and second discs to skin of a human body.

BRIEF DESCRIPTION OF THE DRAWINGS

The above and other objects, features and advantages of the present invention will become more apparent from the following detailed description when taken in conjunction with the accompanying drawings in which.

DETAILED DESCRIPTION OF THE PREFERRED EMBODIMENT

Several preferred embodiments of the present invention will now be described in detail with reference to the annexed drawings. In the following description, a detailed description of known functions and configurations incorporated herein has been omitted for conciseness.

The present invention relates to a composition and method for administration of a solution to a user using either a radial appliance or a wet cell battery appliance for treating yeast and other fungal infections.

Figure 1:
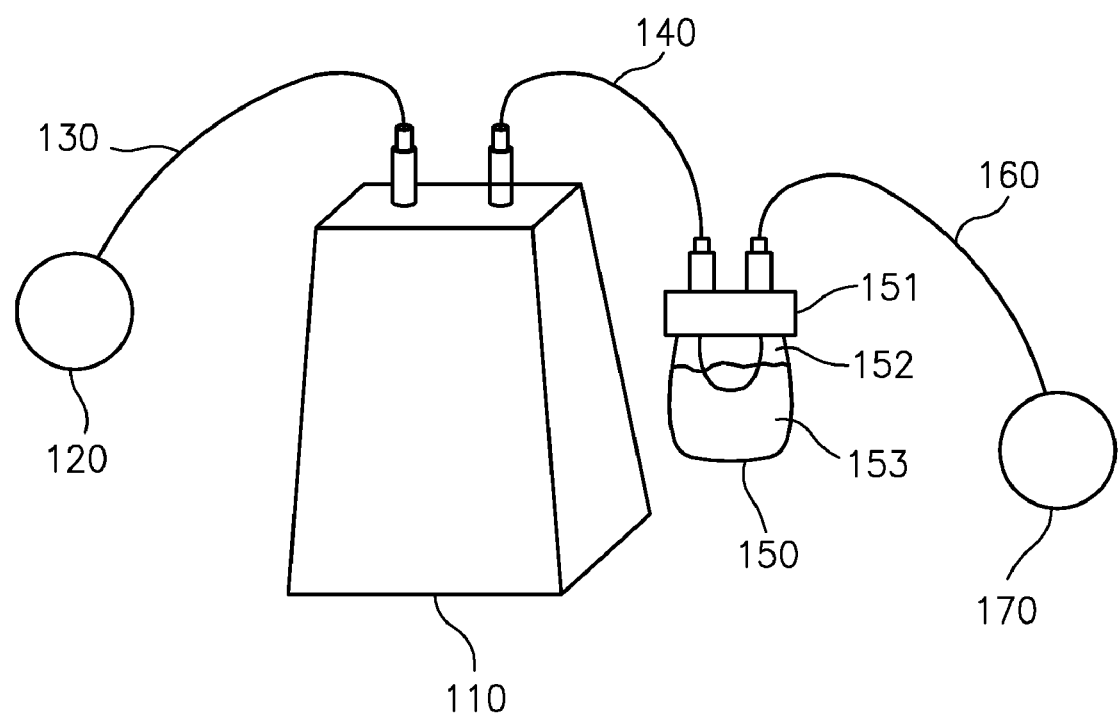
FIG. 1 is a diagram of a conventional radial appliance and solution jar set.
Figure 2:
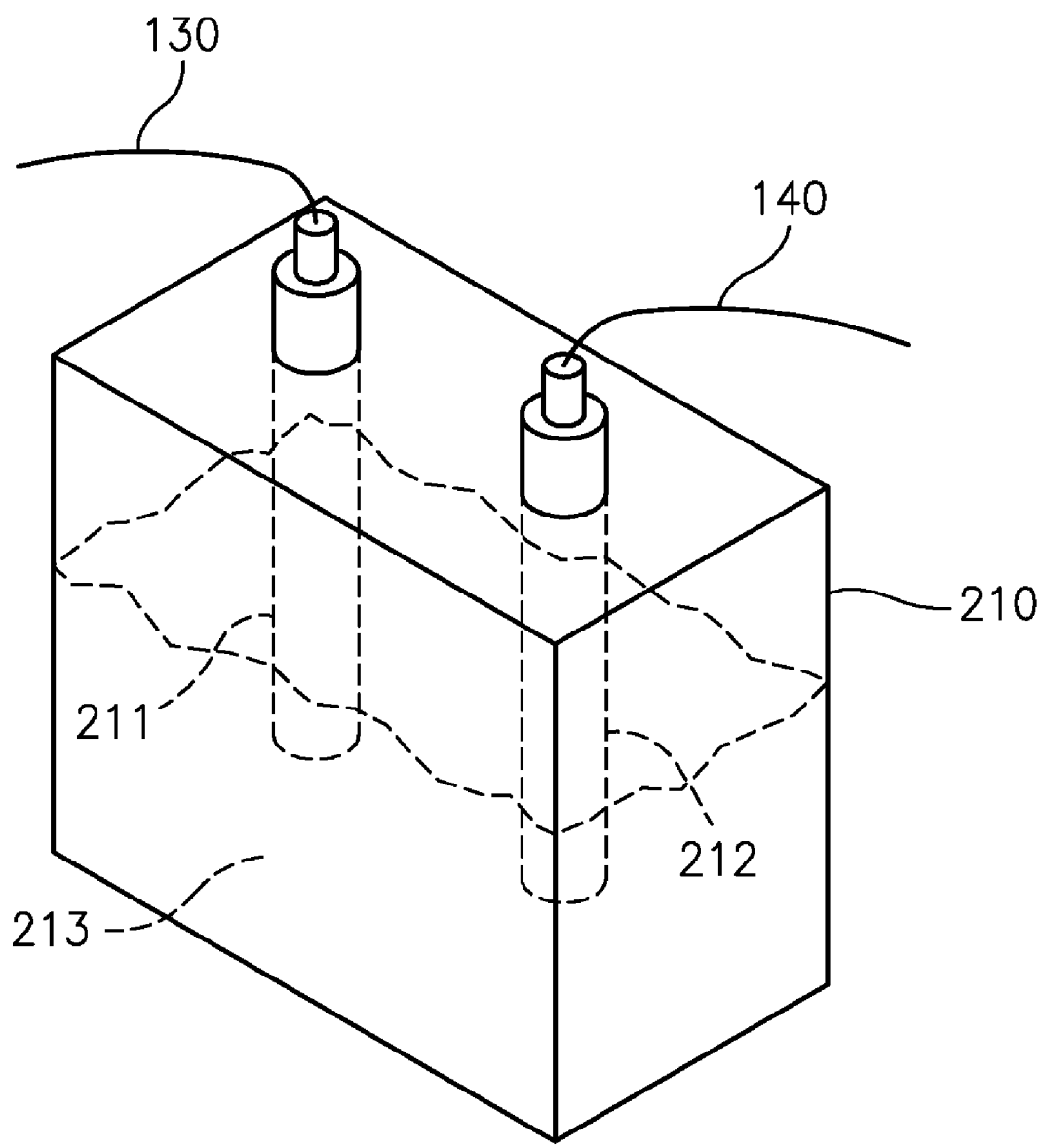
FIG. 2 is a diagram of a conventional wet-cell battery appliance.

A first exemplary embodiment of the present invention is described with reference to FIGS. 1 and 2. According to the first embodiment of the invention, the radial appliance 110 or wet-cell battery appliance 210 is used in conjunction with the solution jar 150.

The solution 153 is a garlic solution comprising garlic extract, ethanol, and water; a 10-undecenoic acid solution comprising 10-undecenoic acid and at least one of alcohol and water; and a Pau d'Arco solution comprising Pau d'Arco extract, corn starch, ethanol, and water. The term "alcohol", as used herein, refers to rubbing alcohol, the specific contents of which are well-known in the art. The garlic solution comprises about 10 percent volume to about 90 percent volume of the solution 153; the 10-undecenoic acid solution comprises about 10 percent volume to about 90 percent volume of the solution 153; and the Pau d'Arco solution comprises about 10 percent volume to about 90 percent volume of the solution 153.

The garlic solution comprises about 1 gram of garlic extract for every 1 mL of the garlic solution. The Pau d'Arco solution comprises about 1 gram of Pau d'Arco extract for every 2 mL of Pau d'Arco solution. According to another exemplary embodiment of the present invention, the solution 153 may also include yerba mate extract.

The solution 153 is placed in the solution jar 150 and administered by applying the first and second discs 120 and 140, respectively in contact with the skin of a user. Garlic is known for treatment of yeast organisms and many fungi. Pau d'Arco is also known for treatment of yeast as well as inhibiting and destroying gram positive bacteria, acid fast bacteria, yeast, Candida, fungi, and viruses. Both ingredients are also known for supporting immune system functions. 10-undecenoic acid is also known for treatment of Candida.

According to a second exemplary embodiment of the present invention, the composition and method of the first exemplary embodiment are used in conjunction with an oral supplementation regimen as follows:

(1) garlic tablets comprising garlic extract administered three times daily;
(2) lactic acid yeast wafers comprising corn, milk whey, malt syrup, *Saccharomyces cerevisiae* yeast, glycerin, honey, arabic gum, cellulose, and calcium stearate, administered six times daily for one month and then administered anytime or twice daily for maintenance;
(3) a first herbal supplement (hereinafter, "VITANOX®") comprising rosemary leaf extract, green tea leaf extract, tumeric rhizome extract, *Vitis vinifera* seed extract, calcium acid phosphate, cellulose, hypromellose, magnesium stearate, silica, and sodium starch glycollate, administered three times daily;
(4) a second herbal supplement (hereinafter, "CAT'S CLAW COMPLEX") comprising cat's claw inner stem bark extract, Pau d'Arco stem bark extract, *echinacea* root extract, calcium acid phosphate, cellulose, corn starch, hypromellose, magnesium stearate, maltodextrin, silica, and sodium starch glycollate, administered 4 times daily; and
(5) oral gel capsules comprising 10-undecenoic acid and olive oil, administered four to six times daily for one month.

The compositions of each of the separately listed herbal supplements (1)-(5) are well-known in the art, and therefore a detailed description thereof is omitted for clarity.

According to third and fourth exemplary embodiments of the present invention, the compositions and methods of the first and second exemplary embodiments, respectively, are used in conjunction with a vaginal irrigation regimen as follows:

Cleansing the vaginal tract for vaginal yeast using, as a douche, a composition including two cups of water, 1 teaspoon to 1 tablespoon of apple cider vinegar, 1 teaspoon of goldenseal extract, 1 teaspoon of Pau d'Arco solution, and 1 teaspoon of oregano oil, daily for one day to four weeks according to the severity of the yeast infection.

All of the ingredients in the above-described vaginal irrigation composition are known for treatment of yeast, except for apple cider vinegar, which is known for cleansing and adjusting pH levels of environments where administered. The compositions of the ingredients of the vaginal irrigation solution are well-known in the art, and therefore a detailed description thereof is omitted for clarity.

While the invention has been shown and described with reference to a certain preferred embodiment thereof, it will be understood by those skilled in the art that various changes in form and details may be made therein without departing from the spirit and scope of the invention as defined by the appended claims.

What is claimed is:

1. A kit for administering a composition to a user through a solution jar assembly, said kit comprising:
 (1) a first composition comprising at least one of:
   a garlic solution comprising garlic extract, ethanol, and water;
   a 10-undecenoic acid solution comprising 10-undecenoic acid and at least one of water and alcohol; and
   a Pau d'Arco solution comprising Pau d'Arco extract, corn starch, ethanol, and water;
 (2) the solution jar assembly comprising:
   a device comprising either a radial appliance or a wet-cell battery appliance;
   a first metal disc connected to the device by a first wire;
   a solution jar, connected to the device by a second wire, for holding the solution;
   a second metal disc connected to the solution jar by a third wire; and
   a connecting loop, located inside the solution jar, connecting the first and third wires and passing through the solution; and
 (3) a second composition comprising at least one of:
   oral tablets comprising garlic extract;
   oral gel capsules comprising 10-undecenoic acid and olive oil;
   lactic acid yeast wafers comprising corn, milk whey, malt syrup, *Saccharomyces cerevisiae* yeast, glycerin, honey, arabic gum, cellulose, and calcium stearate;
   a herbal supplement comprising rosemary leaf extract, green tea leaf extract, tumeric rhizome extract, *Vitis vinifera* seed extract, calcium acid phosphate, cellulose, hypromellose, magnesium stearate, silica, and sodium starch glycollate; and
   a herbal supplement comprising cat's claw inner stem bark extract, Pau d'Arco stem bark extract, *Echinacea* root extract, calcium acid phosphate, cellulose: corn starch, hypromellose, magnesium stearate, maltodextrin, silica, and sodium starch glycollate.

2. The kit according to claim 1, wherein the first composition further comprises yerba mate extract.

3. The kit according to claim 1, wherein the garlic solution comprises about 1 gram of garlic extract for every 1 mL of the garlic solution.

4. The kit according to claim 1, wherein the Pau d'Arco solution comprises about 1 gram of Pau d'Arco extract for every 2 mL of Pau d'Arco solution.

5. The kit according to claim 1, wherein:
the garlic solution comprises about 10 percent volume to about 90 percent volume of the first composition.

6. The kit according to claim 1, wherein:
the Pau d'Arco solution comprises about 10 percent volume to about 90 percent volume of the first composition.

7. The kit according to claim 1, wherein:
the 10-undecenoic acid solution comprises about 10 percent volume to about 90 percent volume of the first composition.

8. The kit according to claim 1, further comprising a third composition, the third composition comprising:
water;
apple cider vinegar;
goldenseal extract;
Pau d'Arco solution; and
oregano oil.

9. A kit for administering a composition to a user through a solution jar assembly, said kit comprising:
(1) the first composition comprising at least one of:
a garlic solution comprising garlic extract, ethanol, and water;
a 10-undecenoic acid solution comprising 10-undecenoic acid and at least one of water and alcohol;
a Pau d'Arco solution comprising Pau d'Arco extract, corn starch, ethanol, and water; and
(2) the solution jar assembly comprising:
a device comprising either a radial appliance or a wet-cell battery appliance;
a first metal disc connected to the device by a first wire;
a solution jar, connected to the device by a second wire, for holding the solution;
a second metal disc connected to the solution jar by a third wire; and
a connecting loop, located inside the solution jar, connecting the first and third wires and passing through the solution; and
(3) a second composition comprising:
water;
apple cider vinegar;
goldenseal extract;
Pau d'Arco solution; and
oregano oil.

10. The kit according to claim 9, wherein the first composition further comprises yerba mate extract.

11. The kit according to claim 9, wherein the garlic solution comprises about 1 gram of garlic extract for every 1 mL of the garlic solution.

12. The kit according to claim 9, wherein the Pau d'Arco solution comprises about 1 gram of Pau d'Arco extract for every 2 mL of Pau d'Arco solution.

13. The kit according to claim 9, wherein:
the garlic solution comprises about 10 percent volume to about 90 percent volume of the first composition.

14. The kit according to claim 9, wherein:
the Pau d'Arco solution comprises about 10 percent volume to about 90 percent volume of the first composition.

15. The kit according to claim 9, wherein:
the 10-undecenoic acid solution comprises about 10 percent volume to about 90 percent volume of the first composition.

* * * * *